(12) United States Patent
Ansmann et al.

(10) Patent No.: US 6,264,961 B1
(45) Date of Patent: Jul. 24, 2001

(54) OIL-WATER EMULSIFIERS

(75) Inventors: Achim Ansmann, Erkrath; Rolf Kawa, Monheim; Helga Gondek, Duesseldorf; Josef Koester, Duesseldorf; Annette Kreisig, Duesseldorf, all of (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/029,774

(22) PCT Filed: Sep. 2, 1996

(86) PCT No.: PCT/EP96/03837
  § 371 Date: Mar. 11, 1998
  § 102(e) Date: Mar. 11, 1998

(87) PCT Pub. No.: WO97/10049
  PCT Pub. Date: Mar. 20, 1997

(30) Foreign Application Priority Data

Sep. 11, 1995 (DE) ............... 195 33 539

(51) Int. Cl.$^7$ .............. A61K 9/00; A61K 9/107
(52) U.S. Cl. .......... 424/401; 252/352; 252/358
(58) Field of Search ............ 424/78.08, 401

(56) References Cited

U.S. PATENT DOCUMENTS

| | | | |
|---|---|---|---|
| 1,985,424 | 12/1934 | Piggott | 260/124 |
| 2,016,962 | 10/1935 | Flint et al. | 260/127 |
| 2,703,798 | 3/1955 | Schwartz | 260/211 |
| 4,931,210 | 6/1990 | Takahashi et al. | 252/314 |
| 4,971,721 | 11/1990 | Takahashi et al. | 252/314 |
| 4,985,173 | 1/1991 | Takahashi et al. | 252/314 |
| 4,988,456 | 1/1991 | Takahashi et al. | 252/314 |
| 5,009,814 | 4/1991 | Kelkenberg et al. | 252/548 |
| 5,374,716 | 12/1994 | Biermann et al. | 536/18.6 |
| 5,391,321 | 2/1995 | Grüning et al. | 252/309 |
| 5,576,425 | 11/1996 | Hill et al. | 436/18.6 |
| 5,712,235 | * 1/1998 | Nieendick et al. | 510/151 |

FOREIGN PATENT DOCUMENTS

| | | |
|---|---|---|
| 20 24 051 | 12/1971 | (DE). |
| 40 29 323 | 3/1992 | (DE). |
| 41 17 033 | 11/1992 | (DE). |
| 42 29 442 | 3/1994 | (DE). |
| 42 36 958 | 8/1994 | (DE). |
| 43 09 567 | 9/1994 | (DE). |
| 44 00 632 | 3/1995 | (DE). |
| 44 14 815 | 11/1995 | (DE). |
| 0 000 424 | 1/1979 | (EP). |
| 0 285 768 | 10/1988 | (EP). |
| 0 301 298 | 2/1989 | (EP). |
| 0 440 203 | 8/1991 | (EP). |
| 0 553 241 | 8/1993 | (EP). |
| 0 559 013 | 9/1993 | (EP). |
| 1 580 491 | 9/1969 | (FR). |
| 1 333 475 | 10/1973 | (GB). |
| 1 524 782 | 9/1978 | (GB). |
| WO85/04346 | 10/1985 | (WO). |
| WO90/03977 | 4/1990 | (WO). |
| WO92/06152 | 4/1992 | (WO). |
| WO92/06153 | 4/1992 | (WO). |
| WO92/06154 | 4/1992 | (WO). |
| WO92/06155 | 4/1992 | (WO). |
| WO92/06156 | 4/1992 | (WO). |
| WO92/06157 | 4/1992 | (WO). |
| WO92/06158 | 4/1992 | (WO). |
| WO92/06159 | 4/1992 | (WO). |
| WO92/06160 | 4/1992 | (WO). |
| WO92/06161 | 4/1992 | (WO). |
| WO92/06162 | 4/1992 | (WO). |
| WO92/06164 | 4/1992 | (WO). |
| WO92/06170 | 4/1992 | (WO). |
| WO92/06171 | 4/1992 | (WO). |
| WO92/06172 | 4/1992 | (WO). |
| WO92/06984 | 4/1992 | (WO). |
| WO95/14549 | 6/1995 | (WO). |
| WO95/34528 | 12/1995 | (WO). |

OTHER PUBLICATIONS

Tens. Surf. Det. 25:8–13 (1988).
J. Am. Oil.Chem. Soc. 49:143 (1972).
"Kosmetische Färbemittel" der Farbstoffkommission der Deutschen Forschungsgemeinschaft, Verlag Chemie p81–106 (1984).

* cited by examiner

*Primary Examiner*—Peter F. Kulkosky
(74) *Attorney, Agent, or Firm*—John E. Drach; Real J. Grandmaison; Steven J. Trzaska

(57) ABSTRACT

The invention relates to new liquid and readily pumpable o/w emulsifiers containing
  a1) alkyl and/or alkenyl oligoglycosides,
  a2) fatty acid N-alkyl polyhydroxyalkylamides and/or
  a3) acyl glutamates and
  b) polyol polyhydroxystearates,
with the proviso that the ratio by weight of a) to b) is in the range from 90:10 to 10:90.

16 Claims, No Drawings

OIL-WATER EMULSIFIERS

BACKGROUND OF THE INVENTION

1. Field of the Invention

This invention relates to new o/w emulsifiers containing selected surfactants in combination with certain polymers and to their use for the production of cosmetic or pharmaceutical formulations.

2. Discussion of Related Art

Polyglycerol polyricinoleates have long been known as emulsifiers and may be used for the formulation of low-viscosity emulsions [cf. EP-A1 0559013 (Th. Goldschmidt), EP-A1 0440203 (Lotte Co.) and WO 85/04346 (Meiji Milk Prods.)]. However, it has been found that commercially available polyglycerol polyricinoleates do not form emulsions with all the oils typically used in cosmetics, but only with those within a certain polarity range. In addition, these emulsions show limited stability in storage. A major disadvantage is, above all, that the commercially available products are not capable of sufficiently stabilizing emulsions containing highly polar oils, for example vegetable oils. In view of the particular ecotoxicological compatibility of such emulsions, however, this is very much a market requirement.

European patent EP-B1 0 553 241 (SEPPIC) also describes self-emulsifying mixtures containing alkyl polyglucosides and fatty alcohols of corresponding chain length. However, where emulsifiers such as these are used, unwanted changes in viscosity over the storage time are observed in many cases.

Now, the problem addressed by the present invention was to provide new ethylene-oxide-free o/w emulsifiers which would form storable emulsions with a broad range of oils.

DESCRIPTION OF THE INVENTION

The present invention relates to o/w emulsifiers containing a1) alkyl and/or alkenyl oligoglycosides,
a2) fatty acid N-alkyl polyhydroxyalkylamides and/or
a3) acyl glutamates and
b) polyol polyhydroxystearates, with the proviso that the ratio by weight of a) to b) is in the range from 90:10 to 10:90, preferably in the range from 70:30 to 30:70 and more preferably in the range from 60:40 to 40:60.

It has surprisingly been found that, where mixtures of the above-mentioned surfactants, preferably $C_{12/14}$ alkyl oligoglucosides, with polyol polyhydroxystearates, preferably polyglycerol poly-12-hydroxystearates, are used as o/w emulsifiers, the emulsions obtained are stable in storage, even in the event of temperature variations, irrespective of the polarity of the oil used. The invention includes the observation that the mixtures are liquid and readily pumpable, particularly when at least one polyol, preferably glycerol, is used as an additional component.

Alkyl and/or Alkenyl Oligoglycosides

Alkyl and alkenyl oligoglycosides are known nonionic surfactants which correspond to formula (I):

where $R^1$ is an alkyl and/or alkenyl radical containing 4 to 22 carbon atoms, G is a sugar unit containing 5 or 6 carbon atoms and p is a number of 1 to 10. They may be obtained by the relevant methods of preparative organic chemistry. EP-A1-0 301 298 and WO 90/03977 are cited as representative of the extensive literature available on this subject.

The alkyl and/or alkenyl oligoglycosides may be derived from aldoses or ketoses containing 5 or 6 carbon atoms, preferably glucose. Accordingly, the preferred alkyl and/or alkenyl oligoglycosides are alkyl and/or alkenyl oligoglucosides.

The index p in general formula (I) indicates the degree of oligomerization (DP degree), i.e. the distribution of mono- and oligoglycosides, and is a number of 1 to 10. Whereas p in a given compound must always be an integer and, above all, may assume a value of 1 to 6, the value p for a certain alkyl oligoglycoside is an analytically determined calculated quantity which is generally a broken number. Alkyl and/or alkenyl oligoglycosides having an average degree of oligomerization p of 1.1 to 3.0 are preferably used. Alkyl and/or alkenyl oligoglycosides having a degree of oligomerization of less than 1.7 and, more particularly, between 1.2 and 1.4 are preferred from the applicational point of view.

The alkyl or alkenyl radical $R^1$ may be derived from primary alcohols containing 4 to 11 and preferably 8 to 10 carbon atoms. Typical examples are butanol, caproic alcohol, caprylic alcohol, capric alcohol and undecyl alcohol and the technical mixtures thereof obtained, for example, in the hydrogenation of technical fatty acid methyl esters or in the hydrogenation of aldehydes from Roelen's oxosynthesis. Alkyl oligoglucosides having a chain length of $C_8$ to $C_{10}$ (DP=1 to 3), which are obtained as first runnings in the separation of technical $C_{8-18}$ coconut oil fatty alcohol by distillation and which may contain less than 6% by weight of $C_{12}$ alcohol as an impurity, and also alkyl oligoglucosides based on technical $C_{9/11}$ oxoalcohols (DP=1 to 3) are preferred.

In addition, the alkyl or alkenyl radical $R^1$ may also be derived from primary alcohols containing 12 to 22 and preferably 12 to 14 carbon atoms. Typical examples are lauryl alcohol, myristyl alcohol, cetyl alcohol, palmitoleyl alcohol, stearyl alcohol, isostearyl alcohol, oleyl alcohol, elaidyl alcohol, petroselinyl alcohol, arachyl alcohol, gadoleyl alcohol, behenyl alcohol, erucyl alcohol, brassidyl alcohol and technical mixtures thereof which may be obtained as described above. Alkyl oligoglucosides based on hydrogenated $C_{12/14}$ coconut oil fatty alcohol having a DP of 1 to 3 are preferred.

Fatty Acid N-alkyl Polyhydroxyalkylamides

Fatty acid N-alkyl polyhydroxyalkylamides are nonionic surfactants which correspond to formula (II):

where $R^2CO$ is an aliphatic acyl radical containing 6 to 22 carbon atoms, $R^3$ is hydrogen, an alkyl or hydroxyalkyl radical containing 1 to 4 carbon atoms and [Z] is a linear or branched polyhydroxyalkyl radical containing 3 to 12 carbon atoms and 3 to 10 hydroxyl groups.

The fatty acid N-alkyl polyhydroxyalkylamides are known compounds which may normally be obtained by reductive amination of a reducing sugar with ammonia, an alkylamine or an alkanolamine and subsequent acylation with a fatty acid, a fatty acid alkyl ester or a fatty acid chloride. Processes for their production are described in U.S. Pat. Nos. 1,985,424, 2,016,962 and 2,703,798 and in International patent application WO 92/06984. An overview of this subject by H. Kelkenberg can be found in Tens. Surf. Det. 25, 8 (1988). The fatty acid N-alkyl polyhydroxyalkylamides are preferably derived from reducing sugars containing 5 or 6 carbon atoms, more particularly from glucose. Accordingly, the preferred fatty acid N-alkyl polyhydroxyalkylamides are fatty acid N-alkyl glucamides which correspond to formula (III):

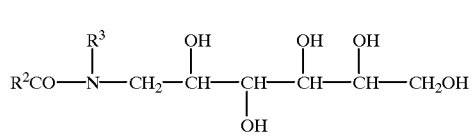

(III)

Preferred fatty acid N-alkyl polyhydroxyalkylamides are glucamides corresponding to formula (III) in which $R^3$ is hydrogen or an alkyl group and $R^2CO$ represents the acyl component of caproic acid, caprylic acid, capric acid, lauric acid, myristic acid, palmitic acid, palmitoleic acid, stearic acid, isostearic acid, oleic acid, elaidic acid, petroselic acid, linoleic acid, linolenic acid, arachic acid, gadoleic acid, behenic acid or erucic acid or technical mixtures thereof. Fatty acid N-alkyl glucamides (III) obtained by reductive amination of glucose with methylamine and subsequent acylation with lauric acid or $C_{12/14}$ coconut oil fatty acid or a corresponding derivative are particularly preferred. In addition, the polyhydroxyalkylamides may also be derived from maltose and palatinose.

The use of fatty acid N-alkyl polyhydroxyalkylamides is also the subject of a number of publications. For example, their use as thickeners is known from European patent application EP-A1 0 285 768 (Hüls). FR-A 1 580 491 (Henkel) describes water-containing detergent mixtures based on sulfates and/or sulfonates, nonionic surfactants and optionally soaps which contain fatty acid N-alkyl glucamides as foam regulators. Mixtures of short-chain and relatively long-chain glucamides are described in DE-C1 44 00 632 (Henkel). In addition, DE-A1 42 36 958 and DE-A1 43 09 567 (Henkel) report on the use of glucamides with relatively long alkyl chains as pseudoceramides in skin-care formulations and on combinations of glucamides with protein hydrolyzates and cationic surfactants in hair-care products.

International patent applications WO 92/06153; WO 92/06156; WO 92/06157; WO 92/06158; WO 92/06159 and WO 92/06160 (Procter & Gamble) describe mixtures of fatty acid-N-alkyl glucamides with anionic surfactants, surfactants of sulfate and/or sulfonate structure, ether carboxylic acids, ether sulfates, methyl ester sulfonates and nonionic surfactants. The use of these substances in various laundry detergents, dishwashing detergents and cleaning products is described in International patent applications WO 92/06152; WO 92/06154; WO 92/06155; WO 92/06161; WO 92/06162; WO 92/06164; WO 92/06170; WO 92/06171 and WO 92/06172 (Procter & Gamble).

Acyl Glutamates

Acyl glutamates are known anionic surfactants corresponding to formula (IV):

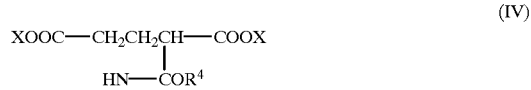

(IV)

in which $R^4CO$ is a linear or branched acyl radical containing 6 to 22 carbon atoms and 0 and/or 1, 2 or 3 double bonds and X is hydrogen, an alkali metal and/or alkaline earth metal, ammonium, alkylammonium, alkanolammonium or glucammonium. They are produced, for example, by Schotten-Baumann acylation of glutamic acid with fatty acids, fatty acid esters or chlorides. Corresponding commercial products are available, for example, from Hoechst AG, Frankfurt, FRG or from the Ajinomoto Co. Inc., Tokyo, JP. An overview of the production and properties of acyl glutamates was published by M. Takehara et al. in J. Am. Oil. Chem. Soc., 49, 143 (1972). Typical examples of suitable acyl glutamates suitable for the purposes of the invention are anionic surfactants derived from fatty acids containing 6 to 22 and preferably 12 to 18 carbon atoms, for example $C_{12/14}$ or $C_{12/18}$ cocofatty acid, lauric acid, myristic acid, palmitic acid and/or stearic acid. Sodium or potassium N-cocoyl and sodium or potassium N-stearoyl-L-glutamate are particularly preferred.

Polyol Polyhydroxystearates

Polyol polyhydroxystearates are esters of polyols and polyhydroxystearic acids. The polyol component may be derived, for example, from glycerol, ethylene glycol, diethylene glycol, propylene glycol, polyglycerol, trimethylol ethane, trimethylol propane, trimethylol butane, pentaerythritol, dipentaerythritol, methyl and butyl glucoside, sorbitol, mannitol, glucose, sucrose or glucamine. Corresponding substances are known, for example, from GB-A 1,524,782 or EP-A-0 000 424.

The substances of component b) are preferably polyglycerol polyhydroxy stearates which are obtained by esterifying polyhydroxystearic acid with a degree of self-condensation of 2 to 20 and preferably 2 to 10 with a polyglycerol mixture having the following preferred composition (gas chromatography):

glycerol: 5 to 35 (15 to 30) % by weight
diglycerols: 15 to 40 (20 to 32) % by weight
triglycerols: 10 to 35 (15 to 25) % by weight
tetraglycerols: 5 to 20 ( 8 to 15) % by weight
pentaglycerols: 2 to 10 ( 3 to 8) % by weight
oligoglycerols: to 100% by weight by methods known per se. The preferred ranges are shown in brackets. The polyol polyhydroxystearates may be produced by methods known per se. In the case of the polyglycerol polyhydroxystearates, the polyglycerol and the polyhydroxystearic acid are preferably produced in that order and, finally, both are esterified. A polyglycerol with the composition indicated above may be prepared by self-condensation of glycerol in the presence of suitable catalysts, for example potassium carbonate, silicates according to DE-A1 40 29 323 (Henkel) or borates according to DE-A1 41 17 033 (Henkel) at temperatures of 200 to 260° C. The polyhydroxystearic acid is produced, for example, by alkali-catalyzed polycondensation of hydroxystearic acid, preferably 12-hydroxystearic acid, which is obtained by hydrogenation of ricinoleic acid or technical castor oil fatty acid. Linear esterification products containing 2 to 10 and, more particularly, 2 to 8 fatty acid units are preferably formed. The following distribution (GPC method) is typically achieved:

monomers: 1 to 10% by weight
dimers: 5 to 15% by weight
trimers: 5 to 15% by weight
tetramers: 5 to 15% by weight
pentamers: 5 to 15% by weight
hexamers: 5 to 15% by weight
heptamers: 5 to 15% by weight
octamers: 1 to 10% by weight
oligomers: to 100 % by weight One particular embodiment of the invention is characterized by the use of mixtures of hydroxystearic acid and ricinoleic acid or technical castor oil fatty acid, of which around 90% by weight consists of ricinoleic acid, in a ratio by weight of 99:1 to 1:99 and preferably 75:25 to 10:90. Similarly, the acids may be individually condensed and the resulting condensates mixed. A complex mixture of homologous polyesters is formed in the subsequent condensation of the polyol component, for example the polyglycerol, with the polyhydroxystearic acid or the mixtures with polyricinoleic acid. The percentage contents of mono-, di-, tri- and oligoesters in the polyol polyhydroxystearates and preferably polyglycerol polyhydroxystearates according to the invention are determined by the ratios in which the starting compounds are used. In one preferred embodiment of the process according to the invention, a polyol polyhydroxystearate with particularly advantageous performance properties is obtained by subjecting around 1000 kg of 12-hydroxystearic acid to self-condensation until a product with an acid value of 50 to 55 is obtained and esterifying the resulting product with around 150 kg of polyglycerol having the composition indicated above until the acid value has fallen to a value below 2. Condensation products based on polyglycerol and polyhydroxystearic acid or polyhydroxystearic acid/polyricinoleic acid may be characterized by their iodine value. Typical examples are polyesters with an iodine value below 10 (basis 100% 12-hydroxystearic acid) or 65 to 80 (basis 90% 12-hydroxystearic acid, 10% ricinoleic acid).

Polyols

Polyols suitable in accordance with the invention as further constituents of the new emulsifiers contain 2 to 15 carbon atoms and at least two hydroxyl groups. Typical examples are glycerol;

alkylene glycols, for example ethylene glycol, diethylene glycol, propylene glycol, polyethylene or polypropylene glycols with molecular weights of 100 to 1000 dalton;

technical oligoglycerol mixtures with a degree of self-condensation of 1.5 to 10, for example technical diglycerol mixtures with a diglycerol content of 40 to 50% by weight;

methylol compounds such as, in particular, trimethylol ethane, trimethylol propane, trimethylol butane, pentaerythritol and dipentaerythritol;

lower alkyl glucosides, especially those containing 1 to 8 carbon atoms in the alkyl radical, for example methyl and butyl glucoside;

sugar alcohols containing 5 to 12 carbon atoms, for example sorbitol or mannitol;

sugars containing 5 to 12 carbon atoms, for example glucose or sucrose;

amino sugars, for example glucamine.

The percentage content of polyols, preferably glycerol, in the new o/w emulsifiers may be 5 to 30% by weight and is preferably 15 to 25% by weight, based on the emulsifiers.

COMMERCIAL APPLICATIONS

The new o/w emulsifiers are particularly suitable for the production of heat-stable and storable emulsions, irrespective of the polarity of the oil component to be emulsified. More particularly, emulsions with a satisfactorily high viscosity can also be produced quickly and reliably using oils of very high polarity.

The present invention also relates to the use of the new o/w emulsifiers for the production of cosmetic and/or pharmaceutical formulations, for example cremes, lotions, emollients and the like.

The emulsions obtainable using the o/w emulsifiers according to the invention may contain further auxiliaries and additives, for example surfactants, oils, co-emulsifiers, superfatting agents, fats, waxes, stabilizers, biogenic agents, preservatives, dyes and perfumes.

The emulsions may contain surfactants compatible with their other ingredients. Typical examples are fatty alcohol polyglycol ether sulfates, monoglyceride sulfates, mono- and/or dialkyl sulfosuccinates, fatty acid isethionates, fatty acid sarcosinates, fatty acid taurides, ether carboxylic acids, alkyl amidobetaines and/or vegetable protein fatty acid condensates.

Suitable oils are, for example, Guerbet alcohols based on fatty alcohols containing 6 to 18 and preferably 8 to 10 carbon atoms, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer diol) and/or Guerbet alcohols, triglycerides based on $C_{6-10}$ fatty acids, vegetable oils, branched primary alcohols, substituted cyclohexanes, Guerbet carbonates, dialkyl ethers and/or aliphatic or naphthenic hydrocarbons.

Nonionic, ampholytic and/or zwitterionic surface-active compounds distinguished by a lipophilic, preferably linear, alkyl or alkenyl group and at least one hydrophilic group may be used as co-emulsifiers. The hydrophilic group may be both an ionic group and a nonionic group.

Nonionic emulsifiers contain, for example, a polyol group, a polyalkylene glycol ether group or a combination of a polyol and a polyglycol ether group as the hydrophilic group. Preferred formulations are those containing nonionic surfactants from at least one of the following groups as o/w emulsifiers: (a1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group; (a2) $C_{12/18}$ fatty acid monoesters and diesters of adducts of 1 to 30 moles of ethylene oxide with glycerol; (a3) glycerol monoesters and diesters and sorbitan monoesters and diesters of saturated and unsaturated fatty acids containing 6 to 22 carbon atoms and ethylene oxide adducts thereof; (a4) ethoxylated alkyl mono- and -oligoglycosides containing 8 to 22 carbon atoms in the alkyl radical and (a5) adducts of 15 to 60 moles of ethylene oxide with castor oil and/or hydrogenated castor oil. Mixtures of compounds from several of these classes are also suitable. The addition products of ethylene oxide and/or propylene oxide with fatty alcohols, fatty acids, alkylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051. In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocoamidopropyl Betaine is particularly preferred. Ampholytic surfactants are also suitable emulsifiers. Ampholytic surfactants are surface-active compounds which, in addition to a $C_{8/18}$ alkyl or acyl group, contain at least one free amino group and at least one —COOH— or —SO$_3$H— group in the molecule and which are capable of forming inner salts. Examples of suitable ampholytic surfactants are N-alkyl glycines, N-alkyl propionic acids, N-alkylaminobutyric acids, N-alkyliminodipropionic acids, N-hydroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine.

Superfatting agents may be selected from such substances as, for example, polyethoxylated lanolin derivatives, lecithin derivatives, polyol fatty acid esters, monoglycerides and fatty acid alkanolamides, the fatty acid alkanolamides also serving as foam stabilizers. Typical examples of fats are glycerides while suitable waxes are inter alia beeswax, paraffin wax or microwaxes, optionally in combination with hydrophilic waxes, for example cetostearyl alcohol and/or partial glycerides of palmitic or stearic acid. Metal salts of fatty acids, for example magnesium, aluminum and/or zinc stearate, may be used as stabilizers. In the context of the invention, biogenic agents are, for example, plant extracts and vitamin complexes. Suitable preservatives are, for example, phenoxyethanol, formaldehyde solution, parabens, pentanediol or sorbic acid while suitable pearlescers include, for example, glycol distearic acid esters, such as ethylene glycol distearate, and fatty acid monoglycol esters. The dyes used may be selected from any of the substances which are permitted and suitable for cosmetic purposes, as listed for example in the publication "Kosmetische Färbemittel" of the Farbstoffkommission der Deutschen Forschungsgemeinschaft, published by Verlag Chemie, Weinheim, 1984, pages 81–106. These dyes are typically used in concentrations of 0.001 to 0.1 % by weight, based on the mixture as a whole.

The total percentage content of auxiliaries and additives may be 1 to 50% by weight and is preferably 5 to 40% by weight, based on the formulation. The formulations may be produced in known manner, i.e. for example by hot, cold, hot-hot/cold or PIT emulsification. These are purely mechanical processes which do not involve a chemical reaction.

EXAMPLES

Examples 1 to 9

Nine exemplary formulations were prepared using a mixture of $C_{12/14}$ cocoalkyl oligoglucoside (Plantaren® APG 1200, Henkel KGaA, Düsseldorf, FRG) and polyglycerol poly-12-hydroxystearate (Dehymuls® PGPH, Henkel KGaA) in a ratio by weight of 60:40 (Examples F1 to F5) or 40:60 (Example F6 to F9). To this end, in the "cold" process (process A), phase I was homogeneously stirred at 20° C., phase II was slowly added with stirring, phase III was then stirred in and homogenized and, finally, phase IV was added. In the hot process (process B), phase I was heated to 85° C. and homogeneously stirred, preheated phase II was added and the emulsion was subsequently cooled. The composition of the emulsions is given in Table 1:

TABLE 1

Composition of Exemplary Formulations

Exemplary Formulations (% by weight)

| Phase | Components (CTFA) | F1 | F2 | F3 | F4 | F5 | F6 | F7 | F8 | F9 |
|---|---|---|---|---|---|---|---|---|---|---|
| I | O/W emulsifier | 2.9 | 2.4 | 2.4 | 3.1 | 4.0 | 6.4 | 6.4 | 6.4 | 3.3 |
|  | PEG-20 Glyceryl Stearate | — | 1.6 | 1.6 | — | — | — | — | — | — |
|  | Sodium Laureth Sulfate | — | — | — | 2.3 | — | — | — | — | — |
|  | Glycerol (99%) | — | — | — | — | — | 4.0 | — | 4.0 | — |
|  | Propylene glycol | — | — | — | — | — | — | 4.0 | — | — |
|  | Cetearyl Alcohol | — | — | — | — | — | — | — | 5.5 | — |
|  | Caprylic Capric Triglyceride | 16.0 | 16.0 | — | 16.0 | — | 16.0 | 16.0 | 16.0 | 16.0 |
|  | Paraffin oil, low-viscosity | — | — | 16.0 | — | 16.0 | — | — | — | — |
| II | Water, dist. |  |  |  |  | ad 100 |  |  |  |  |
|  | Glycerol (99%) | 3.0 | 3.0 | 3.0 | 3.0 | 3.0 | — | — | — | 3.0 |
|  | Sodium chloride | — | — | — | — | — | — | — | — | 5.0 |
| III | Polymer Carbopol ® 980 (2%) | 15.0 | 15.0 | 15.0 | 15.0 | 15.0 | 15.0 | 15.0 | — | — |
|  | Keltrol ® BT | — | — | — | — | — | — | — | — | 1.5 |
| IV | Potassium hydroxide (20%) | 0.5 | 0.5 | 0.5 | 0.5 | 0.5 | 0.5 | 0.5 | — | 0.5 |
|  | pH value |  |  |  |  | 6.6 |  |  |  |  |
|  | Viscosity* [Pas] | 18 | 39 | >40 | 12 | 11 | 24 | 24 | 8 | 14 |
|  | Production process | A | A | A | A | A | A | A | B | A |

Storable emulsions with a Brookfield viscosity (RFV, 23° C., 10 r.p.m., spindle 5 or 6 in Ex. F3) of 5 to 50,000 mPas were obtained.

Examples 10 to 13, Comparison Examples C1 and C2

Mixtures containing 20% by weight of almond oil, 7% by weight of emulsifier, 5% by weight of glycerol (86% by weight) and 5% by weight of magnesium sulfate-7-hydrate (water to 100% by weight) were prepared, stored for 4 weeks and their viscosity subsequently determined. The following emulsifiers were tested:

A1) Plantaren® APG 1200/Dehymuls® PGPH=60:40
A2) Plantaren® APG 1200/Dehymuls® PGPH=40:60
A3) Plantaren® APG 1200/Dehymuls® PGPH/glycerol= 25:50:25

A4) Lauric acid-N-methyl glucamidelDehymuls® PGPH= 60:40
B1) Polyglycerol polyricinoleate
B2) Glycerol poly-1 2-hydroxystearate The results are set out in Table 2:

TABLE 2

Viscosity and Stability of Emulsions Containing Polar Oils

| Example Emulsifier | Viscosity [mPas] After | | | Stability After | |
|---|---|---|---|---|---|
| | 1 Day | 1 Week | 4 Weeks | 1 Day | 4 Weeks |
| 10) A1 | 24000 | 23000 | 23000 | Stable | Stable |
| 11) A2 | 23500 | 22000 | 20000 | Stable | Stable |
| 12) A3 | 19500 | 19000 | 19000 | Stable | Stable |
| 13) A4 | 25000 | 24000 | 23500 | Stable | Stable |
| C1) B1 | — | — | — | Does not emulsify | |
| C2) B2 | — | — | — | Does not emulsify | |

Examples 14 and 15, Comparison Examples C3 and C4

Two emulsions were prepared by the hot method using the emulsifier according to the invention and an ethylene-oxide-containing comparison mixture consisting of Ceteareth-12 and Ceteareth-20. The viscosity of the emulsions was measured by the Brookfield method as described above and was observed over a period of 1 day to 8 weeks. Stability was evaluated at room temperature and 40° C. after 4 weeks and 8 weeks. Formulations F10 and F12 correspond to the invention while formulations F11 and F13 are intended for comparison. The results are set out in Table 3.

TABLE 3

Viscosity and Stability of Emulsions

| Components (CTFA Nomenclature) | Exemplary Formulations (% by weight) | | | |
|---|---|---|---|---|
| | F10 | F11 | F12 | F13 |
| Emulsifier compound | 6.6 | — | — | — |
| Decyl Polyglucose | — | — | 2.4 | — |
| Polyglyceryl Poly-12-hydroxystearate | — | — | 1.2 | — |
| Ceteareth-12 | — | 1.5 | — | 1.5 |
| Ceteareth-20 | — | 1.5 | — | 1.5 |
| Hydrogenated Palm Glycerides | — | — | 8.0 | 8.0 |
| Oleyl Erucate | — | — | 2.0 | 2.0 |
| Decyl Oleate | — | — | 4.0 | 4.0 |
| Dicapryl Ether | — | — | 2.0 | 2.0 |
| Caprylic/Capric Triglyceride | — | — | 4.0 | 4.0 |
| Glyceryl Stearate | 15.0 | 15.0 | — | — |
| Paraffin oil, low-viscosity | 10.0 | 10.0 | — | — |
| Polymer Carbopol® 980 | — | — | 10.0 | 10.0 |
| KOH, 20% by weight | — | — | 0.4 | 0.4 |
| Glycerol | — | 3.0 | 3.0 | 3.0 |
| Water, preservative | To 100% by weight | | | |
| Viscosity [mPas] after | | | | |
| 2 Day | 775,000 | 300,000 | 200,000 | 112,500 |
| 1 Week | 750,000 | 287,500 | 187,000 | 93,750 |
| 4 Weeks | 737,500 | 200,000 | 200,000 | 75,000 |
| 8 Weeks | 750,000 | 150,000 | | |
| Stability after | | | | |
| 4 Weeks (RT) | Stable | Stable | Stable | Stable |
| 4 Weeks (40° C.) | Stable | Stable | Stable | Unstable |
| 8 Weeks (RT) | Stable | Stable | | |
| 8 Weeks (40° C.) | Stable | Stable | | |

*)Emulsifier compound:
18% by weight Polyglyceryl Poly-12-hydroxystearate
36% by weight Decyl Polyglucose
46% by weight glycerol

What is claimed is:

1. An oil-in-water emulsifier composition comprising;
   a1) an alkyl or alkenyl oligoglycosides,
   a2) a fatty acid N-alkyl polyhydroxyalkylamide, or
   a3) an acyl glutamate, and
   b) a polyol polyhydroxystearate,
with the proviso that the ratio by weight of component a) to component b) is from 90:10 to 10:90.

2. An oil-in-water emulsifier composition according to claim 1 wherein said alkyl or alkenyl oligoglycosides corresponds to formula (I):

$$R^1O\text{---}[G]_p \qquad (I)$$

where $R^1$ is an alkyl or alkenyl radical containing 4 to 22 carbon atoms, G is a sugar unit containing 5 or 6 carbon atoms and p is a number of 1 to 10.

3. An oil-in-water emulsifier composition according to claim 1 wherein said fatty acid-N-alkyl polyhydroxyalkylamide corresponds to formula (II):

$$R^2CO\text{---}\underset{\underset{R^3}{|}}{N}\text{---}[Z] \qquad (II)$$

where $R^2CO$ is an aliphatic acyl radical containing 6 to 22 carbon atoms, $R^3$ is hydrogen, an alkyl or hydroxyalkyl radical containing 1 to 4 carbon atoms and Z is a linear or branched polyhydroxyalkyl radical containing 3 to 12 carbon atoms and 3 to 10 hydroxyl groups.

4. An oil-in-water emulsifier composition according to claim 1 wherein said acyl glutamate corresponds to formula (IV):

$$XOOC\text{---}CH_2CH_2\underset{\underset{HN\text{---}COR^4}{|}}{CH}\text{---}COOX \qquad (IV)$$

in which $R^4CO$ is a linear or branched acyl radical containing 6 to 22 carbon atoms and 0, 1, 2 or 3 double bonds and X is hydrogen, an alkali metal or alkaline earth metal, ammonium, alkylammonium, alkanolammonium or glucammonium.

5. An oil-in-water emulsifier composition according to claim 1 wherein said polyol polyhydroxystearate comprises polyglycerol poly-12-hydroxystearate.

6. An oil-in-water emulsifier composition according to claim 1 wherein the ratio by weight of component a) to component b) is from 70:30 to 30:70.

7. An oil-in-water emulsifier composition according to claim 1 further containing a polyol.

8. An oil-in-water emulsifier composition according to claim 7 wherein said polyol is present in an amount of from 5% to 30% by weight, based on the weight of said emulsifier composition.

9. A cosmetic or pharmaceutical composition containing an oil-in-water emulsifier composition comprising;

a1) an alkyl or alkenyl oligoglycosides, a2) a fatty acid N-alkyl polyhydroxyalkylamide, or a3) an acyl glutamate, and b) a polyol polyhydroxystearate, with the proviso that the ratio by weight of component a) to component b) is from 90:10 to 10:90.

10. A cosmetic or pharmaceutical composition according to claim 9 wherein said alkyl or alkenyl oligoglycosides corresponds to formula (I):

(I)

where $R^1$ is an alkyl or alkenyl radical containing 4 to 22 carbon atoms, G is a sugar unit containing 5 or 6 carbon atoms and p is a number of 1 to 10.

11. A cosmetic or pharmaceutical composition according to claim 9 wherein said fatty acid-N-alkyl polyhydroxyalkylamide corresponds to formula (II):

(II)

where $R^2CO$ is an aliphatic acyl radical containing 6 to 22 carbon atoms, $R^3$ is hydrogen, an alkyl or hydroxyalkyl radical containing 1 to 4 carbon atoms and Z is a linear or branched polyhydroxyalkyl radical containing 3 to 12 carbon atoms and 3 to 10 hydroxyl groups.

12. A cosmetic or pharmaceutical composition according to claim 9 wherein said acyl glutamate corresponds to formula (IV):

(IV)

in which $R^4CO$ is a linear or branched acyl radical containing 6 to 22 carbon atoms and 0, 1, 2 or 3 double bonds and X is hydrogen, an alkali metal or alkaline earth metal, ammonium, alkylammonium, alkanolammonium or glucammonium.

13. A cosmetic or pharmaceutical composition according to claim 9 wherein said polyol polyhydroxystearate comprises polyglycerol poly-12-hydroxystearate.

14. A cosmetic or pharmaceutical composition according to claim 9 wherein the ratio by weight of component a) to component b) is from 70:30 to 30:70.

15. A cosmetic or pharmaceutical composition according to claim 9 further containing a polyol.

16. A cosmetic or pharmaceutical composition according to claim 15 wherein said polyol is present in an amount of from 5% to 30% by weight, based on the weight of said emulsifier composition.

* * * * *